US00PP16050P2

(12) United States Plant Patent
Endisch

(10) Patent No.: US PP16,050 P2
(45) Date of Patent: Oct. 18, 2005

(54) ***GERANIUM* PLANT NAMED 'GENSTARED'**

(50) Latin Name: *Pelargonium peltatum*
Varietal Denomination: Genstared

(75) Inventor: Gerd Endisch, Hagenbach (DE)

(73) Assignee: Willi Endisch GbR, Hagenbach (DE)

( * ) Notice: Subject to any disclaimer, the term of this patent is extended or adjusted under 35 U.S.C. 154(b) by 85 days.

(21) Appl. No.: 10/850,199

(22) Filed: May 20, 2004

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Mark P. Bourgeois

(57) ABSTRACT

A new and distinct cultivar of *Geranium* plant named 'Genstared' that is characterized by dark purple-red double flowers, medium to dark green foliage with a light to medium zonation pattern and a medium to late flower response.

1 Drawing Sheet

Botanical classification: *Pelargonium peltatum.*
Variety denomination: 'Genstared'.

BACKGROUND OF THE INVENTION

The present invention relates to a new and distinct cultivar of *Geranium* plant botanically known as *Pelargonium peltatum* and hereinafter referred to by the cultivar name 'Genstared'.

The new cultivar is the product of a breeding program conducted by the inventor in a cultivated area of Hagenbach, Germany. The objective of the breeding program is to develop new *Geranium* cultivars with double flowers, medium green foliage and a medium flower response.

'Genstared' is a hybrid that originated from the hybridization of the female or seed parent a proprietary selection of *Pelargonium peltatum* identified by number D776 (not patented) and the male or pollen parent a proprietary selection of *Pelargonium peltatum* identified as 'Bonete' (not patented). The cultivar 'Genstared' was selected by the inventor in 1999 as a single plant within the progeny of the stated cross in a controlled environment of Hagenbach, Germany.

Asexual reproduction by terminal cuttings of the new cultivar 'Genstared' were taken in 1999 in Hagenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Geranium* cultivar 'Genstared'. These traits in combination distinguish 'Genstared' as a new and distinct cultivar apart from other known existing varieties of *Geranium.*

1. *Geranium 'Genstared' exhibits dark purple-red flowers.*
2. *Geranium 'Genstared' exhibits double flowers.*
3. *Geranium 'Genstared' exhibits medium to dark green foliage with a light to medium zonation pattern.*
4. *Geranium 'Genstared' exhibits a medium to late flower response.*

The closest comparison variety is *Geranium* 'Guija' (not patented). 'Genstared' is different than 'Guija' in having a later flower response and longer leaves.

The new cultivar 'Genstared' is distinguishable from the female parent 'D776' by the following characteristics:

1. 'Genstared' has darker purple-red flowers.
2. 'Genstared' has an earlier flower response.
3. 'Genstared' has darker green leaves with a zonation pattern.

The new cultivar 'Genstared' is distinguishable from the male parent 'Bonete' by the following characteristics:

1. 'Genstared' has darker purple-red flowers.
2. 'Genstared' has a later flower response.
3. 'Genstared' has darker green leaves.
4. 'Genstared' has longer branches.

BRIEF DESCRIPTION OF THE DRAWING

The accompanying photograph illustrates the distinguishing traits of *Geranium* 'Genstared'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Geranium* cultivar named 'Genstared'. Data was collected in Hagenbach, Germany from 12 week old plants grown under glass greenhouse conditions. The plants were grown in 12 cm diameter containers. The time of year was Spring and the daytime temperature ranged from 18 to 26° Centigrade. The temperature at night ranged from 16 to 20° Centigrade. The light level was 20 to 35 klux. No photoperiodic treatments were used. The growth retardant CYCOCEL 720 was applied at a rate of 0.05 percent. Color determinations are in accordance with The Royal Horticultural Society Colour Chart 2001 edition, except where general color terms of ordinary dictionary significance are used. The growing requirements are similar to the species.

'Genstared' has not been tested under all possible conditions and phenotypic differences may be observed with variations in environmental, climatic, and cultural conditions, however, without any variance in genotype.

Botanical classification: *Pelargonium peltatum* cultivar 'Genstared'.
Annual or Perennial: Annual.
Parentage: 'Genstared' is a hybrid plant that resulted from the hybridization of the following parent plants:
*Female parent.*—A proprietary selection of *Pelargonium peltatum* identified as 'D776'.
*Male parent.*—A proprietary selection of *Pelargonium peltatum* identified as 'Bonete'.
Vigor: Moderate.
Growth rate: Approximately 6.5 cm. per month.
Growth habit: Upright, outwardly spreading.
Plant shape: Globose.
Plant height: Average 23 cm. in height.
Plant width: Average 18 cm. in width.
Suitable container size: 10 to 14 cm containers.
Propagation: Terminal cuttings.
Time to initiate roots: Approximately 6–8 days to produce roots on an initial cutting.
Time to produce a rooted cutting or liner: Approximately 20–26 days.
Crop time: From a rooted cutting, approximately 13.5 weeks are required to produce a finished flowering plant.
High temperature tolerance: 40 degrees Centigrade.
Low temperature tolerance: 0 degrees Centigrade.
Root system: Fine and fibrous.
Stem:
*Branching habit.*—Free branching.
*Basal branching.*—Yes.
*Average number of lateral branches.*—6.
*Pinching.*—No.
*Lateral branch dimensions.*—12 cm. in length and 0.4 cm. in diameter.
*Lateral branch strength.*—Moderate.
*Color.*—143B.
*Pubescence.*—Absent.
*Internode length.*—3.0 cm. between nodes.
*Shape.*—Round.
*Surface.*—Glabrous, slightly glossy.
Foliage:
*Texture.*—Both sides smooth.
*Leaf arrangement.*—Alternate.
*Compound or single.*—Single.
*Quantity of leaves per lateral branch.*—6.
*Leaf shape.*—Reniform.
*Leaf apex.*—Rounded.
*Leaf base.*—Cordate.
*Leaf length.*—4 cm. in length.
*Leaf width.*—7.5 cm. in width.
*Pubescence.*—Present on both sides.
*Leaf margin.*—Entire lobed.
*Vein pattern.*—Palmate.
*Young leaf color* (*upper surface*).—137B.
*Young leaf color* (*lower surface*).—137C.
*Mature leaf color* (*upper surface*).—137A.
*Mature leaf color* (*lower surface*).—137B to 137C.
*Vein color* (*upper surface*).—144A.
*Vein color* (*lower surface*).—138B.
*Zonation pattern.*—Moderate presence.
*Zonation color.*—Reddish brown, about 176A.
*Leaf attachment.*—Petiolate.
*Petiole dimensions.*—6.0 cm. in length and 2.8 mm. in width.
*Petiole color.*—144A.
Inflorescence:
*Inflorescence arrangement.*—Rounded hemispherical umbels.
*Inflorescence type.*—Umbel.
*Inflorescence dimensions.*—4.0 cm in height and 7.5 cm in width.
*Flowering habit.*—Continuous.
*Quantity of flowers per inflorescence.*—Approximately 9.
*Quantity of buds per lateral stem.*—Approximately 6.
*Quantity of flowers and buds per plant.*—Approximately 110.
*Flowering season.*—Spring to Summer.
*Time to flower.*—Approximately 8.5 weeks.
*Rate of flower opening.*—Approximately 60% of the flowers are opened at once.
*Fragrance.*—None.
*Bud dimensions.*—6 mm. in length and 3.8 mm. in diameter.
*Bud shape.*—Elliptical.
*Bud color.*—143B.
*Rate of bud opening.*—4 days.
*Flower aspect.*—Upright.
*Flower shape.*—Shallow cup shaped, rounded, double.
*Flower dimensions.*—5.3 cm. in diameter and 2.0 cm. in height.
*Flower longevity.*—Lasts approximately 9 days on plant.
*Petal texture.*—Glabrous.
*Number of petals.*—8.
*Petals fused or unfused.*—Unfused.
*Petal shape.*—Ovate.
*Petal margin.*—Entire.
*Petal apex.*—Rounded.
*Petal base.*—Attenuate.
*Petal dimensions.*—2.4 cm. in length and 2.1 cm. in width.
*Upper petal color when opening* (*upper side*).—53A, three markings above base, 3 mm in length and 1 mm in width, color 59A.
*Lower petal color when opening* (*upper side*).—53A.
*Upper petal color when opening* (*under side*).—53B, three markings above base, 3 mm in length and 1 mm in width, color 59A.
*Lower petal color when opening* (*under side*).—53B.
*Upper petal color fully opened* (*upper side*).—53A, three markings above base, 3 mm in length and 1 mm in width, color 59A.
*Lower petal color fully opened* (*upper side*).—53A.
*Upper petal color fully opened* (*under side*).—53B, three markings above base, 3 mm in length and 1 mm in width, color 59A.
*Lower petal color fully opened* (*under side*).—53B.
*Petaloids.*—4, triangle shaped, 1.4 cm in length and 3 mm in width, color 53A.
Self-cleaning or persistent: Persistent.
Sepals:
*Number of sepals.*—5.
*Sepal surface.*—Upper side: dull and pubescent, Lower side: glabrous.
*Sepal shape.*—Lanceolate.
*Sepal margin.*—Entire.
*Sepal apex.*—Acute.

*Sepal base.*—Cuneate.
*Sepal dimensions.*—1.4 cm. in length and 3.5 mm. in width.
*Sepal color immature* (*upper side*).—143B.
*Sepal color immature* (*under side*).—143B.
*Sepal color mature* (*upper side*).—143B.
*Sepal color mature* (*under side*).—143B.

Peduncle:
*Peduncle dimensions.*—8.0 cm. in length and 3.0 mm. in diameter.
*Peduncle angle.*—15°.
*Peduncle color.*—144A.
*Peduncle strength.*—Moderate.

Pedicels:
*Pedicel dimensions.*—2.3 cm. in length and 1.2 mm. in diameter.
*Pedicel angle.*—20°.
*Pedicel color.*—143A.
*Pedicel strength.*—Moderate.

Reproduction organs:
*Stamen number.*—6.
*Anther shape.*—Ovate.
*Anther dimensions.*—2.5 mm.
*Anther color.*—61B.
*Amount of pollen.*—Moderate.
*Pollen color.*—31A.
*Pistil number.*—1 in number.
*Pistil dimensions.*—8 mm. in length.
*Stigma shape.*—Five parted, star shaped.
*Stigma color.*—46A.
*Style length.*—5 mm.
*Style color.*—46A.
*Ovary color.*—143B.

Seed: Seed production has not been observed.

Disease and pest resistance: Plants of the new *Geranium* have not been observed for disease or pest resistance.

It is claimed:

1. A new and distinct variety of *Geranium* plant named 'Genstared' as described and illustrated.

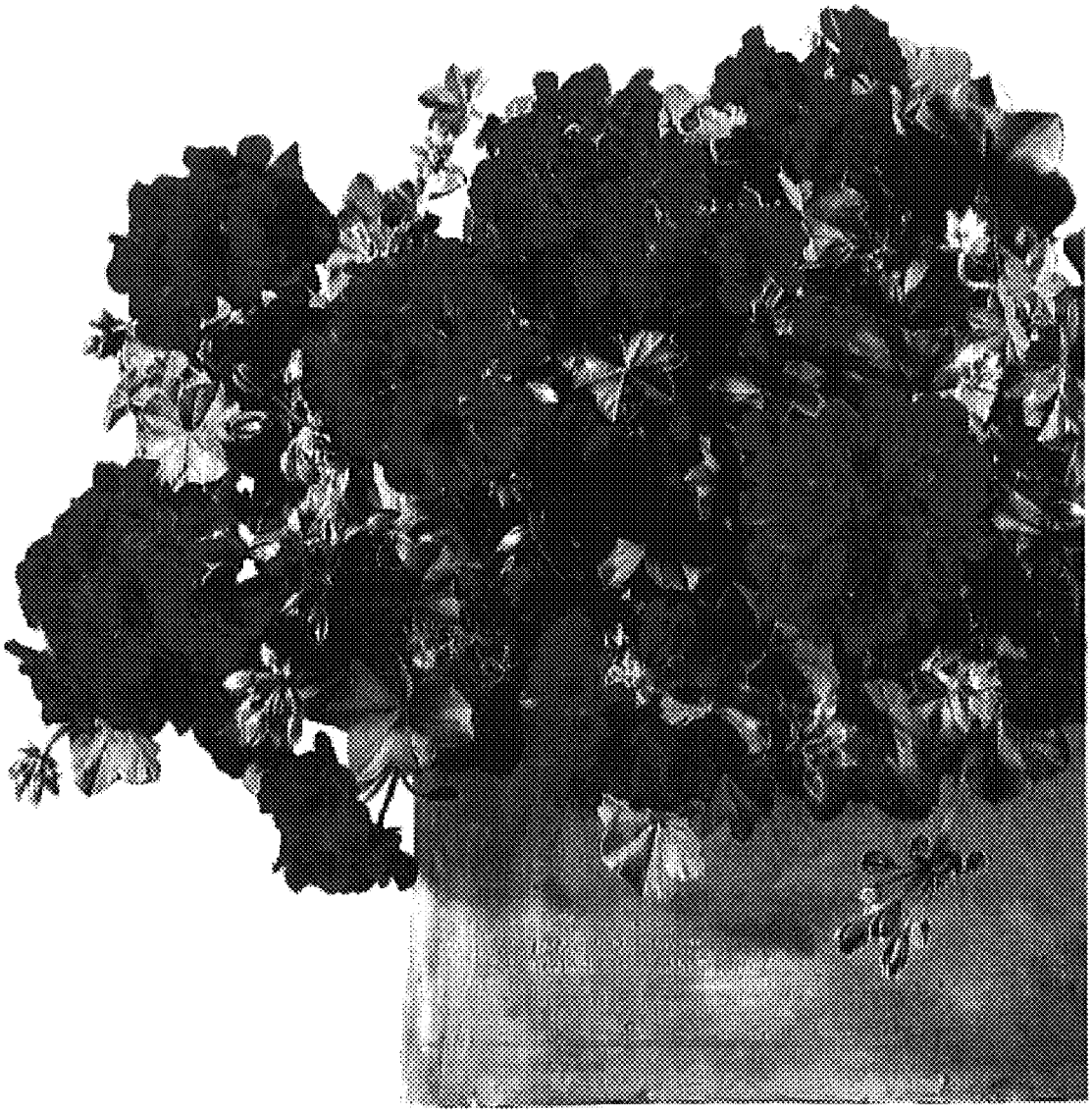

* * * * *